United States Patent
Coker et al.

(10) Patent No.: US 11,779,306 B2
(45) Date of Patent: Oct. 10, 2023

(54) ULTRASONIC CATHETER ASSEMBLY

(71) Applicant: Avent, Inc., Alpharetta, GA (US)

(72) Inventors: Justin Jeffrey Coker, Laguna Niguel, CA (US); Kenneth C. Hsu, Tustin, CA (US); Paul Jun, La Crescenta, CA (US); Steve S. Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 583 days.

(21) Appl. No.: 15/743,900

(22) PCT Filed: Jul. 21, 2015

(86) PCT No.: PCT/US2015/041242
§ 371 (c)(1),
(2) Date: Jan. 11, 2018

(87) PCT Pub. No.: WO2017/014749
PCT Pub. Date: Jan. 26, 2017

(65) Prior Publication Data
US 2018/0199915 A1    Jul. 19, 2018

(51) Int. Cl.
*A61B 8/00* (2006.01)
*A61B 8/12* (2006.01)
(Continued)

(52) U.S. Cl.
CPC ............ *A61B 8/445* (2013.01); *A61B 8/0833* (2013.01); *A61B 8/0841* (2013.01); *A61B 8/12* (2013.01); *A61B 5/06* (2013.01)

(58) Field of Classification Search
None
See application file for complete search history.

(56) References Cited

U.S. PATENT DOCUMENTS

| | | | | |
|---|---|---|---|---|
| 4,576,177 A | * | 3/1986 | Webster, Jr. ......... | A61B 8/0833 600/439 |
| 4,697,595 A | * | 10/1987 | Breyer ................. | A61B 8/0833 600/463 |

(Continued)

FOREIGN PATENT DOCUMENTS

| EP | 2 343 098 A1 | 7/2011 |
|---|---|---|
| EP | 2 540 336 A1 | 1/2013 |

(Continued)

OTHER PUBLICATIONS

Ong et al., "Engineered Piezoelectricity in Graphene", ACS Nano, vol. 6, No. 2, pp. 1387-1394, 2012. (Year: 2012).*

(Continued)

*Primary Examiner* — Katherine L Fernandez
(74) *Attorney, Agent, or Firm* — Dority & Manning, P.A.

(57) ABSTRACT

The present disclosure is directed to an ultrasonic catheter assembly. More specifically, the catheter assembly includes a catheter and one or more piezoelectric or echogenic components. The catheter has a side wall that extends from a proximal end and a distal end that defines a lumen extending from the proximal end to the distal end. Thus, the lumen is configured to deliver a treatment fluid from the proximal end to the distal end. In addition, the piezoelectric component(s) are configured with the side wall of the catheter and/or embedded at least partially within the side wall of the catheter. As such, the piezoelectric component(s) are configured to enhance ultrasonic imaging of the catheter, e.g. when activated by a stimulator assembly.

4 Claims, 7 Drawing Sheets

(51) Int. Cl.
*A61B 8/08* (2006.01)
*A61B 5/06* (2006.01)

(56) References Cited

U.S. PATENT DOCUMENTS

| | | | |
|---|---|---|---|
| 4,969,890 A | 11/1990 | Sugita et al. | |
| 5,081,997 A | 1/1992 | Bosley, Jr. et al. | |
| 5,701,905 A * | 12/1997 | Esch | A61B 5/0215 600/486 |
| 5,747,672 A * | 5/1998 | Parent | G01N 29/032 310/340 |
| 5,759,154 A | 6/1998 | Hoyns | |
| 6,179,809 B1 | 1/2001 | Khairkhahan et al. | |
| 7,226,417 B1 * | 6/2007 | Eberle | B06B 1/0633 29/25.35 |
| 7,438,711 B2 | 10/2008 | Deniega et al. | |
| 7,465,291 B2 | 12/2008 | Massengale | |
| 7,527,609 B2 | 5/2009 | Deniega et al. | |
| 7,569,045 B2 | 8/2009 | Deniega et al. | |
| 8,328,771 B2 | 12/2012 | Massengale | |
| 8,611,993 B2 | 12/2013 | Vitullo et al. | |
| 8,652,098 B2 | 2/2014 | Haslinger | |
| 8,796,908 B2 | 8/2014 | Okuba | |
| 9,802,025 B2 | 10/2017 | Khalaj | |
| 2002/0042564 A1 * | 4/2002 | Cooper | A61F 2/90 600/407 |
| 2002/0142119 A1 | 10/2002 | Seward et al. | |
| 2004/0077948 A1 | 4/2004 | Violante et al. | |
| 2004/0193109 A1 | 9/2004 | Prestidge et al. | |
| 2004/0249288 A1 | 12/2004 | Ichikawa | |
| 2005/0163954 A1 * | 7/2005 | Shaw | A61L 27/10 428/36.1 |
| 2007/0167739 A1 | 7/2007 | Salo | |
| 2008/0058702 A1 | 3/2008 | Arndt et al. | |
| 2009/0105597 A1 * | 4/2009 | Abraham | A61B 8/08 600/466 |
| 2009/0131910 A1 | 5/2009 | Webler | |
| 2011/0066073 A1 * | 3/2011 | Kuiper | A61B 10/0241 600/562 |
| 2011/0172542 A1 | 7/2011 | Racz | |
| 2011/0319758 A1 | 12/2011 | Wang | |
| 2012/0059308 A1 | 3/2012 | Hsu et al. | |
| 2012/0095404 A1 | 4/2012 | Massengale et al. | |
| 2012/0116228 A1 * | 5/2012 | Okubo | A61B 8/00 600/459 |
| 2012/0126663 A1 | 5/2012 | Jenninger et al. | |
| 2013/0223702 A1 | 8/2013 | Holsing et al. | |
| 2013/0310823 A1 * | 11/2013 | Gelfand | A61B 18/18 606/33 |
| 2014/0024928 A1 | 1/2014 | Boctor et al. | |
| 2014/0142509 A1 | 5/2014 | Bonutti et al. | |
| 2014/0214149 A1 * | 7/2014 | Kuraguntla | A61B 5/0031 623/1.15 |
| 2014/0316327 A1 | 10/2014 | Rajendran et al. | |
| 2014/0378841 A1 * | 12/2014 | Coats | A61B 8/445 600/458 |
| 2015/0038378 A1 * | 2/2015 | Cheng | G01N 33/5438 506/39 |

FOREIGN PATENT DOCUMENTS

| | | |
|---|---|---|
| JP | 2001293091 A | 10/2001 |
| JP | 2010279546 A | 12/2010 |
| WO | WO 99/51294 | 10/1999 |
| WO | WO 00/04287 | 7/2000 |
| WO | WO 2009/091514 A2 | 7/2009 |
| WO | WO 2014/174305 A2 | 10/2014 |

OTHER PUBLICATIONS

Stephen M. Klein, M.D., et al., "Piezoelectric Vibrating Needle and Catheter for Enhancing Ultrasound-Guided Peripheral Nerve Blocks", Technical Communication from the International Anesthesia Research Society, vol. 105, No. 6, Dec. 2007, 3 pages.
Co-pending U.S. Appl. No. 15/735,719, filed Dec. 12, 2017.
Co-pending U.S. Appl. No. 15/735,731, filed Dec. 12, 2017.
International Search Report for PCT/US2015/041242, dated Jun. 8, 2016, 5 pages.

* cited by examiner

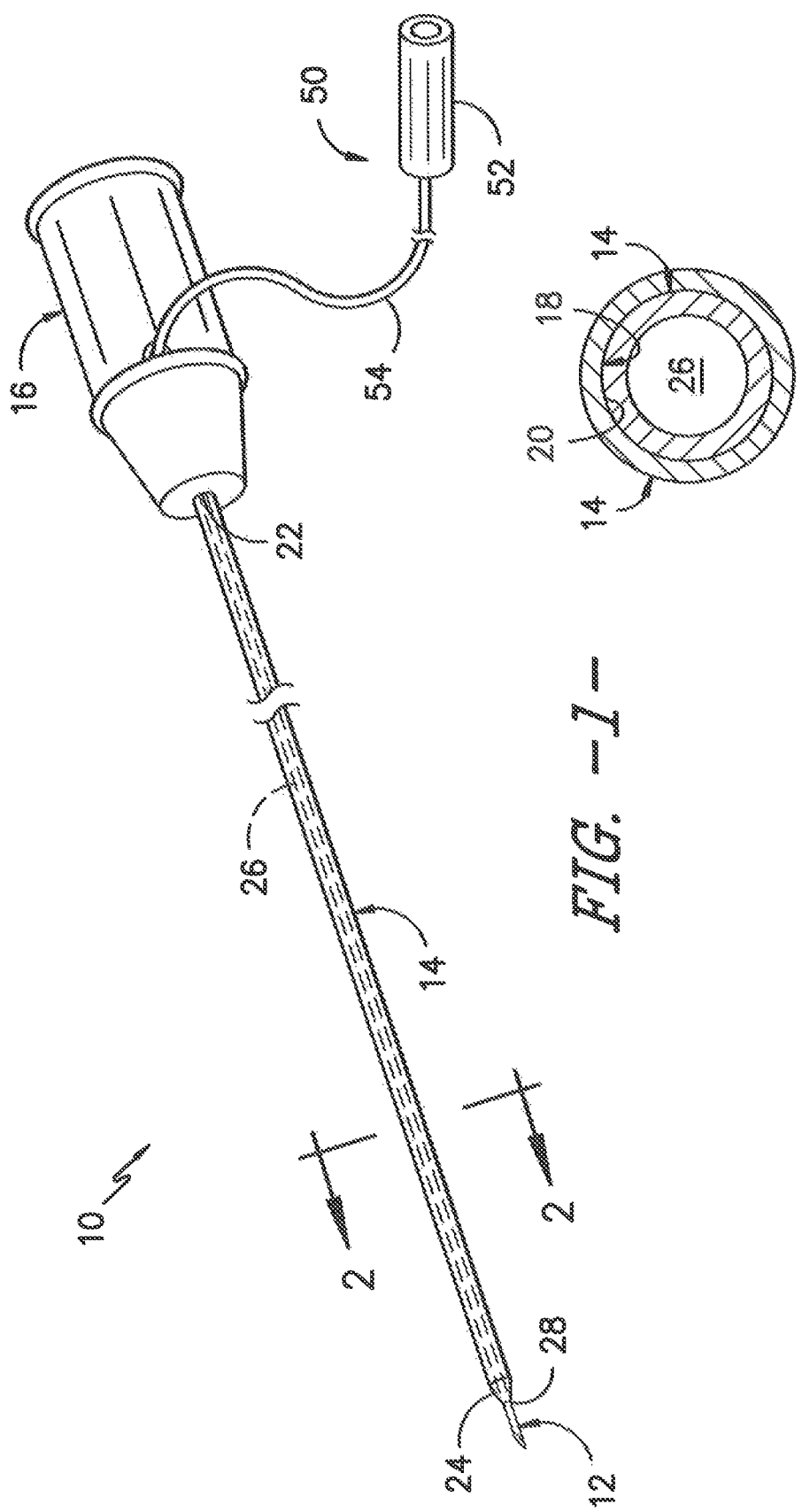

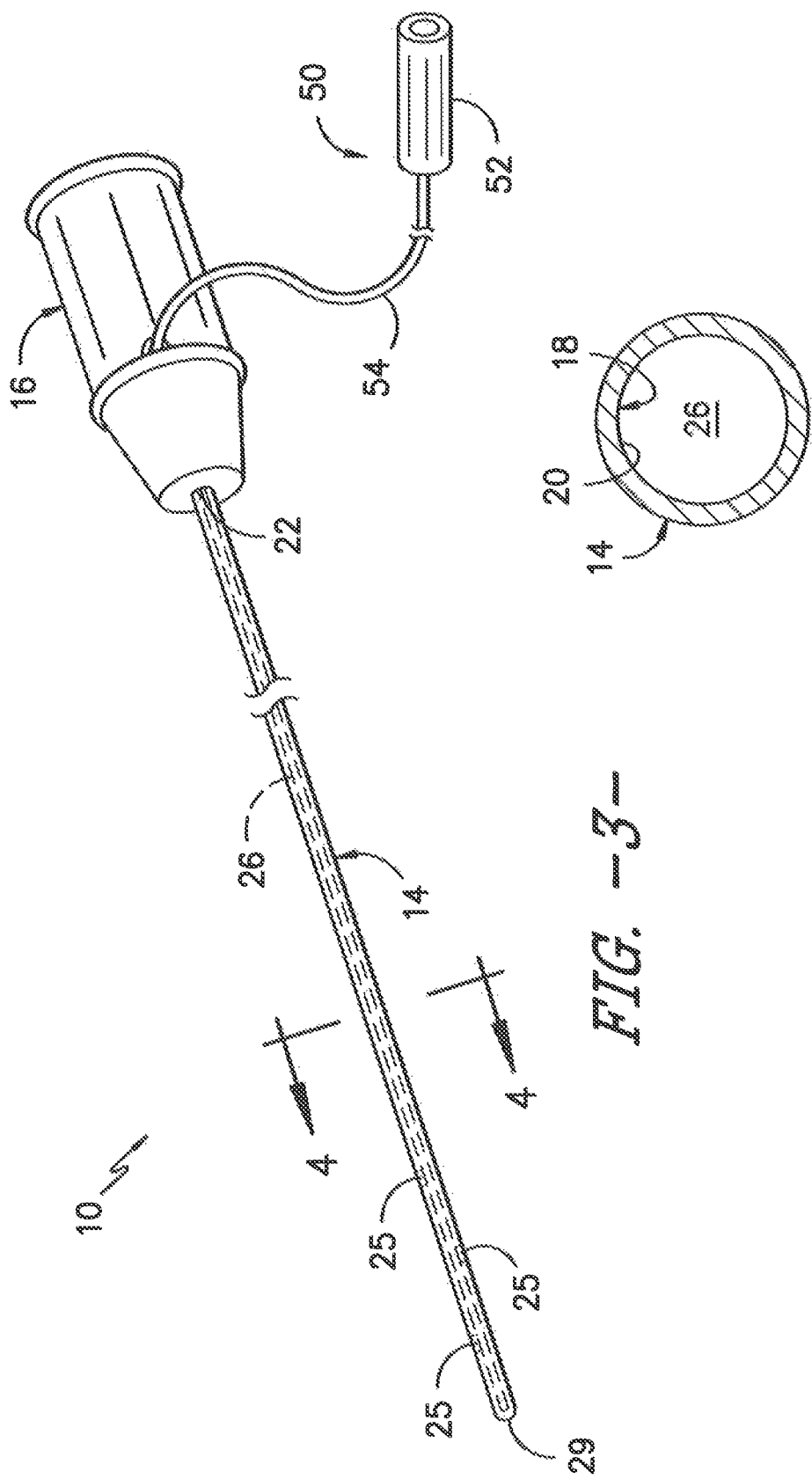

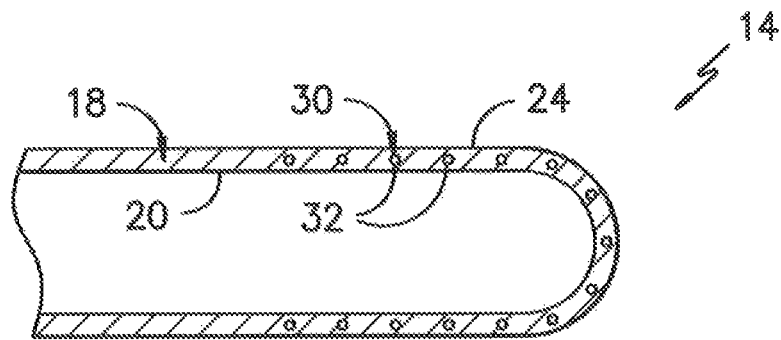
FIG. -5-
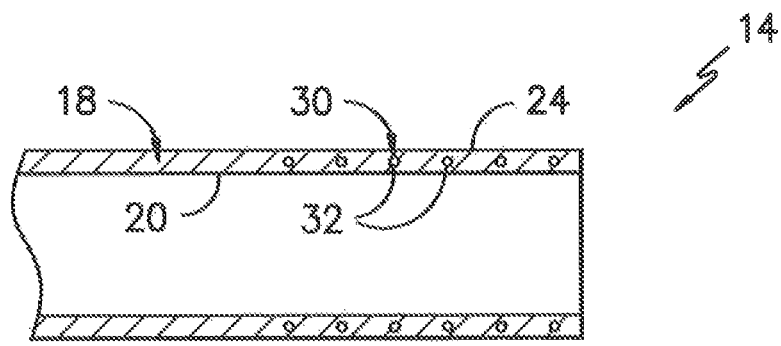
FIG. -6-
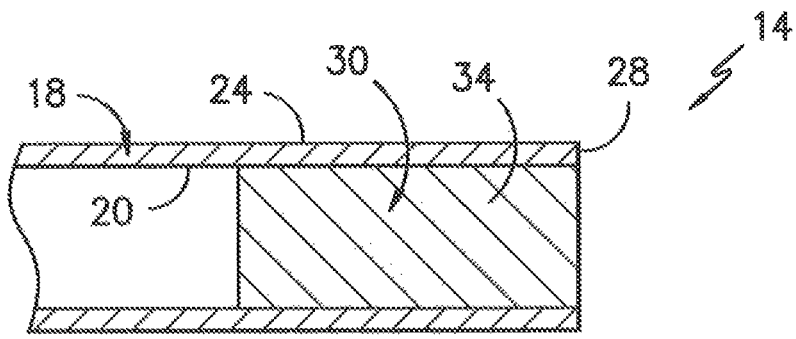
FIG. -7-

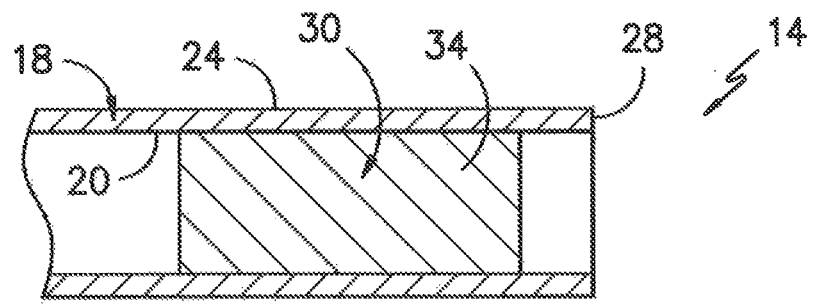
FIG. -8-
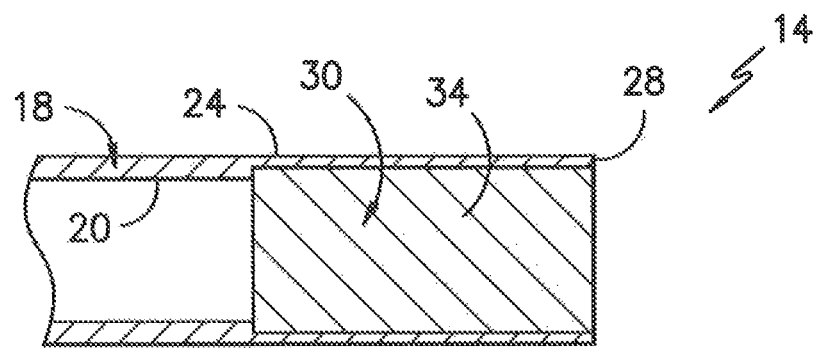
FIG. -9-
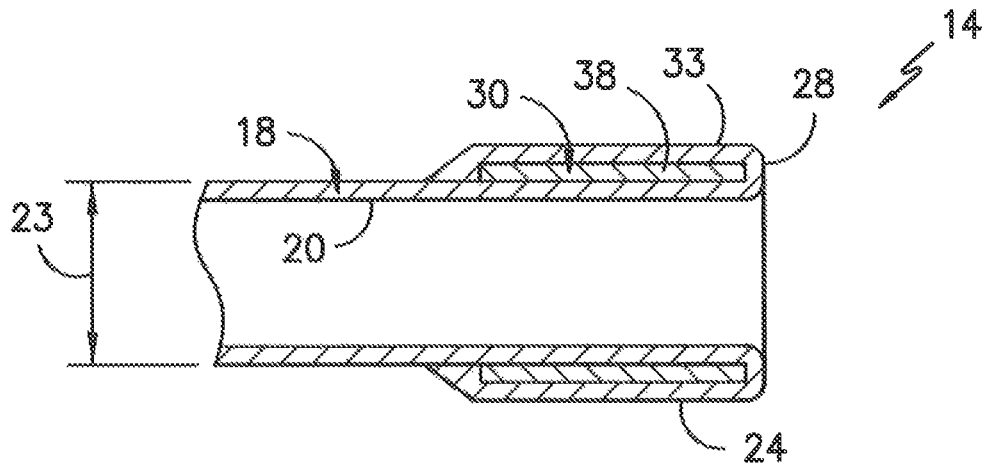
FIG. -10-

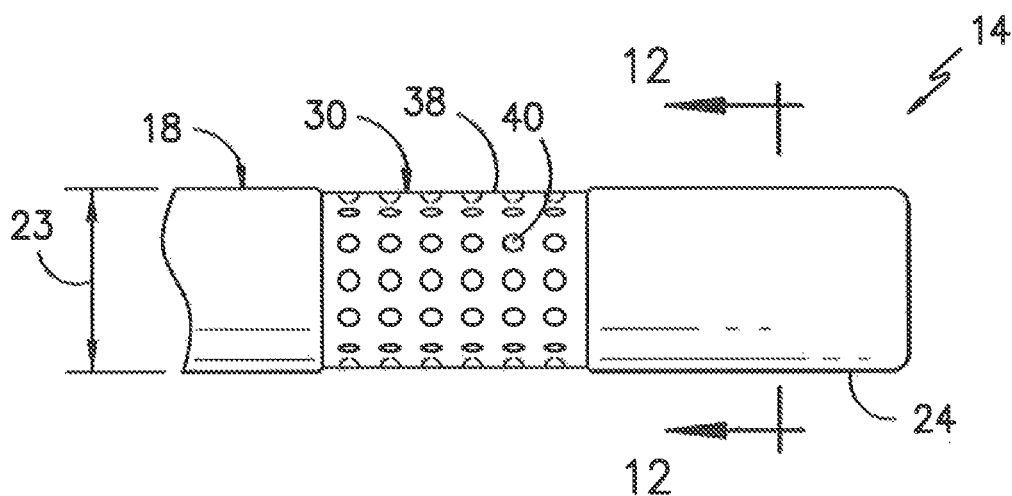
FIG. -11-
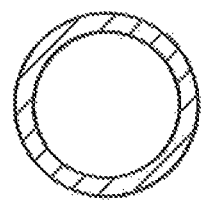
FIG. -12-
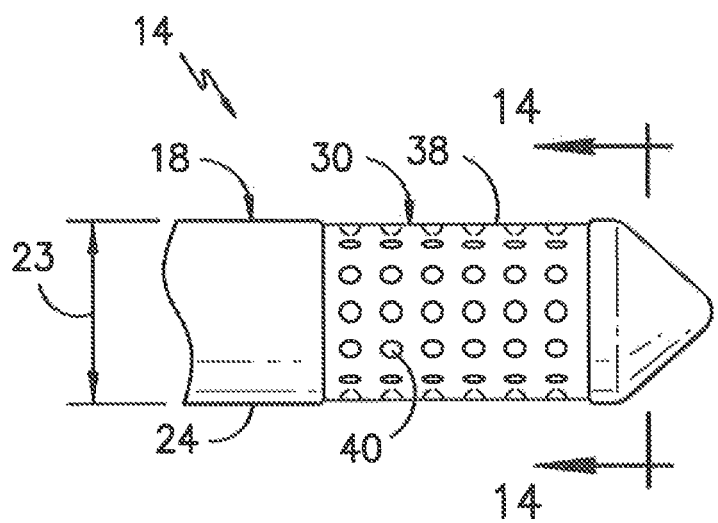
FIG. -13-
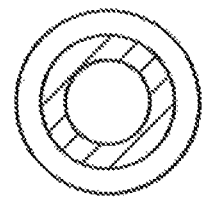
FIG. -14-
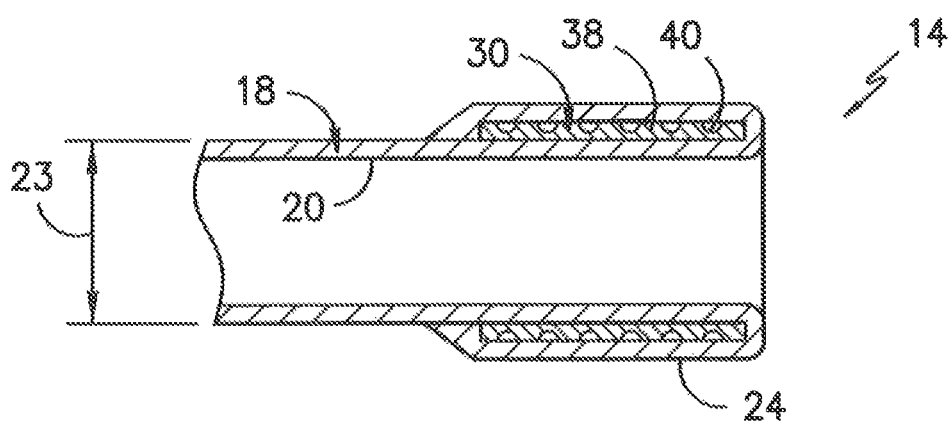
FIG. -15-

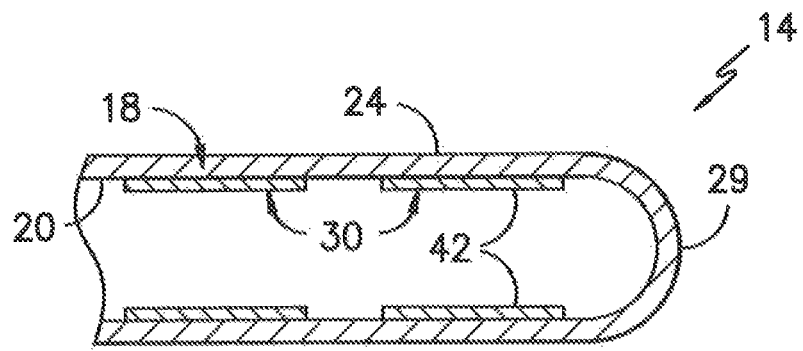
FIG. -16-
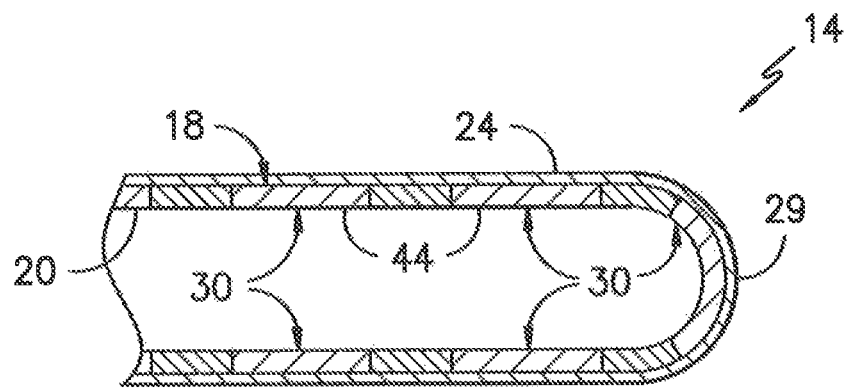
FIG. -17-
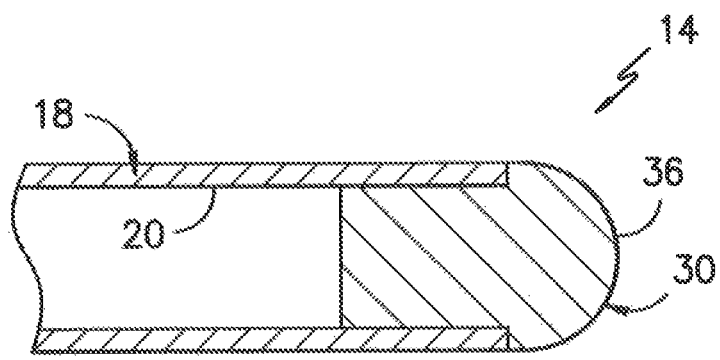
FIG. -18-

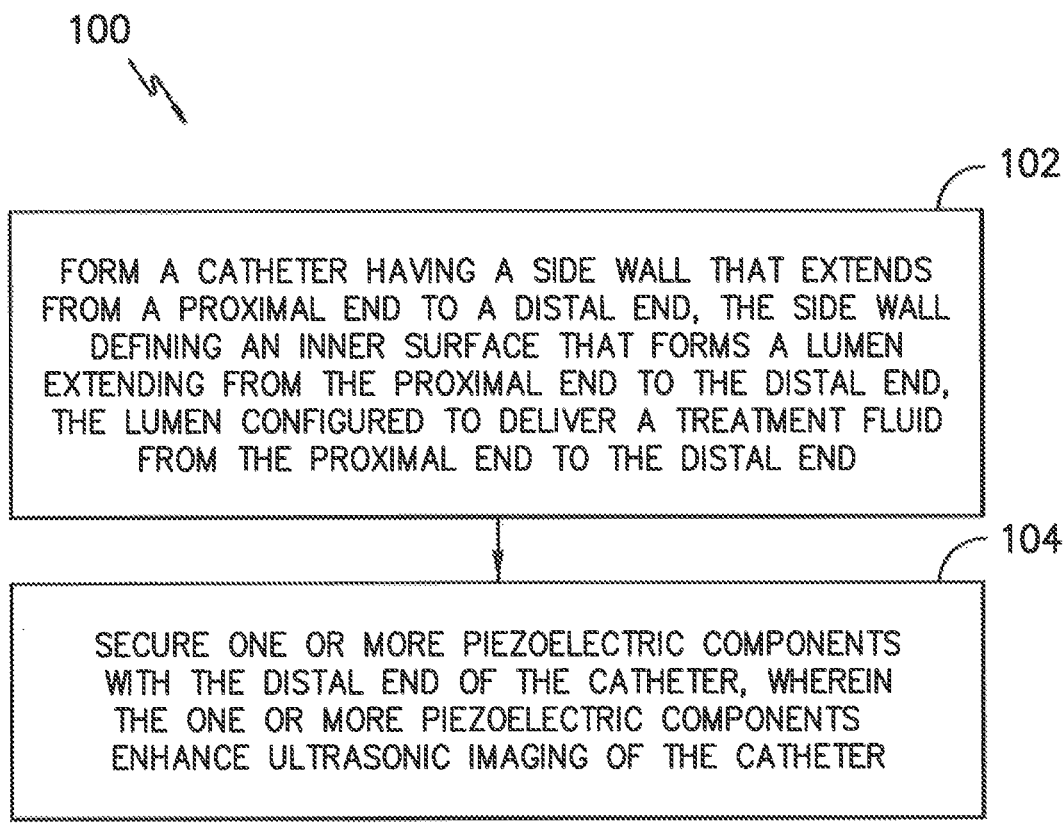
FIG. -19-

ULTRASONIC CATHETER ASSEMBLY

RELATED APPLICATION

The present application is the national stage entry of International Application Number PCT/US2015/041242 filed on Jul. 21, 2015, which is incorporated herein in its entirety by reference hereto.

FIELD OF THE INVENTION

The present invention relates generally to the field of medical catheters and more particularly to a catheter assembly configured to provide enhanced ultrasonic imaging.

BACKGROUND

Prior to performing a surgical operation on a part of the body, it may be desirable to perform a nerve block in order to anesthetize a nerve bundle in a part of the body proximate to where surgery will occur. Often, a catheter-based infusion system is utilized to both block the nerve bundle for surgery and to provide a continuous, low flow rate of the anesthetic over a period of time (e.g., 2-3 days following surgery) for post-operative pain management.

One approach is to introduce an epidural-type needle or needle and peel-away-type sheath into the general area of the desired nerve bundle. Once proper location of the needle is achieved, a test dose of the anesthetic may be provided through the epidural needle and a catheter may be introduced through the needle to administer the anesthetic and maintain the nerve block.

Several methods of targeting needle location exist today, e.g. insulated needles having an integral conductive wire such that a small amount of current may be pulsed through the needle or catheter by a nerve stimulator (i.e., a current generator). An electrical current of 0.1 to about 2 mA will induce motor movement in the patient when the tip of the needle (frequently called a "stimulating needle") is near the nerve. When the stimulating needle is probed into the general area of the desired nerve bundle, the pulsing current stimulates the nerve and causes a motor response to assist in properly locating the needle. As the current is reduced, the motor effect is also reduced so a needle that causes movement at a low current is likely to be very close to the desired area for drug delivery.

One problem with this approach is that catheter insertion through the needle may move the tip of the needle away from the target zone. Alternatively and/or additionally, the tip of the catheter may curl away from the target zone during insertion.

Several manufacturers have designed stimulating catheters that correct this problem by passing the current first through the needle and then separately through the catheter. The problem with this is that the catheter cannot be steered to the target zone without risking pulling back through the needle and potentially damaging the catheter. In addition, the additional time needed to place and maneuver the catheter is significant and after the catheter is secured, it can dislodge by patient movement and become ineffective.

Still another type of catheters, generally referred to as "over-the-needle" (OTN) catheters, may be used to address the issues above. More specifically, OTN catheters include a catheter coaxially mounted onto a needle such that the catheter and the needle may be inserted into a patient together. Once the catheter and the needle are located at the targeted site, the needle can be removed, leaving the catheter in place. Thus, OTN catheters can be purposely directed to a targeted site within a patient without the need to thread the catheter therethrough. Accordingly, OTN catheters have gained increased attention in regard to delivering anesthetic medication, for example, for the purposes of nerve block.

Ultrasound guided techniques have added imaging to such procedures, but they are mainly used to see the adjacent vessels and are not always good at seeing the needle and/or catheter. The problem with ultrasound guided techniques is that the catheter cannot be easily seen through tissue. That is, the ability to see the tip and/or other portions of the catheter under ultrasound imaging techniques is limited. Another problem is that conventional catheters do not allow one to place the catheter quickly allowing for some small migration or tip mis-positioning while still delivering drug to the target area.

Thus, improved catheters that address the aforementioned issues and that can be more easily placed at a treatment site within a patient would be advantageous. Accordingly, the present invention is directed to an ultrasonic catheter that can be easily viewed using ultrasonic imaging.

SUMMARY OF THE INVENTION

Objects and advantages of the invention will be set forth in part in the following description, or may be obvious from the description, or may be learned through practice of the invention.

In one aspect, the present invention is directed to an active ultrasonic catheter assembly. The catheter assembly includes a catheter and one or more piezoelectric components. The catheter has a side wall that extends from a proximal end and a distal end. Further, the side wall defines a lumen extending from the proximal end to the distal end. Thus, the lumen is configured to deliver a treatment fluid from the proximal end to the distal end. In addition, the piezoelectric component(s) are configured with the side wall of the lumen of the catheter. As such, the piezoelectric component(s) are configured to enhance ultrasonic imaging of the catheter.

In one embodiment, the piezoelectric component(s) may be embedded within the side wall of the catheter. In another embodiment, the piezoelectric component(s) may be embedded at the distal end of the catheter. Thus, in certain embodiments, the piezoelectric component(s) may be embedded within the side wall of the catheter such that the one or more piezoelectric components are shielded from a patient when inserted therein.

In further embodiments, the piezoelectric component(s) include at least one of a catheter tip, a catheter plug, a plurality of piezoelectric elements, a catheter band, or similar. In additional embodiments, the piezoelectric component(s) may be constructed, at least in part, of graphene, crystals, ceramics (e.g. ceramic crystals), or any other suitable piezoelectric material. Thus, in certain embodiments, where graphene is used, the graphene may be applied to the catheter in the form of a graphene coating, a graphene strip, or similar. Additionally, the piezoelectric component(s) may have any one of or a combination of the following shapes: sphere, cylinder, cone, pyramid, prism, cube, cuboid, irregular, ring- or band-shaped, or similar.

In yet another embodiment, the active ultrasonic catheter assembly may include a stimulator assembly configured to activate the piezoelectric component(s) when the catheter is inserted into a patient. Thus, the stimulator assembly is configured to enhance ultrasonic imaging of the assembly.

In another aspect, the present disclosure is directed a method of manufacturing an ultrasonic catheter assembly.

The method includes providing a catheter having a side wall that extends from a proximal end to a distal end. The side wall defines an inner surface that forms a lumen extending from the proximal end to the distal end. The lumen is configured to deliver a treatment fluid from the proximal end to the distal end. The method also includes placing one or more echogenic components onto the distal end of the catheter. Thus, the method further includes heating the distal end of the catheter until a portion of the distal end melts and cures over the one or more echogenic components. As such, the portion of the distal end that melts over the one or more echogenic components shields the echogenic components from a patient.

In one embodiment, the echogenic component(s) may include a plurality of discontinuities configured to enhance ultrasonic imaging of the catheter. In another embodiment, the discontinuities may include at least one or more of the following: etchings, indentations, grooves, notches, recesses, threads, protrusions, or similar. Further, in certain embodiments, the echogenic component(s) may include at least one of a catheter tip or a catheter band configured to fit around an outer diameter of the catheter.

In yet another aspect, the present disclosure is directed to a method of manufacturing an active ultrasonic assembly. The method includes providing a catheter having a side wall that extends from a proximal end to a distal end. The side wall of the catheter defines an inner surface that forms a lumen extending from the proximal end to the distal end. Thus, the lumen is configured to deliver a treatment fluid from the proximal end to the distal end. The method also includes securing one or more piezoelectric components with the distal end of the catheter. Thus, the piezoelectric component(s) are configured to enhance ultrasonic imaging of the catheter.

In one embodiment, the piezoelectric component(s) may be configured to contact at least a portion of the inner surface of the catheter. For example, in certain embodiments, the step of securing one or more piezoelectric components with the distal end of the catheter may further include inserting the piezoelectric component(s) (e.g. a catheter tip, a catheter plug, a catheter band, or similar) within the distal end of the catheter such that the piezoelectric component(s) contacts the inner surface of the side wall of the catheter.

In further embodiments, the step of securing one or more piezoelectric components with the distal end of the catheter may further include embedding one or more piezoelectric components into the side wall of the catheter at the distal end thereof. More specifically, in such embodiments, the piezoelectric component(s) may include at least one of a catheter tip, a catheter plug, a plurality of piezoelectric elements, a catheter band, or similar. In additional embodiments, the step of embedding the piezoelectric component(s) into the side wall of the catheter at the distal end may also include placing the piezoelectric component(s) onto the distal end of the catheter and heating the distal end until a portion of the distal end melts and cures over the piezoelectric component(s). As such, the portion of the distal end that melts over the piezoelectric component(s) is configured to shield the piezoelectric component(s) from a patient.

In another embodiment, the step of securing one or more piezoelectric components with the distal end of the catheter may further include applying a graphene coating, one or more graphene strips, or similar to the inner surface of the side wall of the catheter.

In additional embodiments, the method may also include activating, via a stimulator assembly, the piezoelectric component(s) when the catheter is inserted into a patient.

In still another aspect, the present disclosure is directed to a method of manufacturing an ultrasonic catheter assembly. The method includes providing a catheter having a side wall that defines a lumen extending from a proximal end to a distal end. The lumen is configured to deliver a treatment fluid from the proximal end to the distal end. Further, the side wall further defines an outer diameter of the catheter. The method also includes placing one or more echogenic components around the outer diameter of the catheter. Moreover, the echogenic component(s) include a plurality of discontinuities on an outer surface thereof. The method further includes heating the distal end of the catheter until a portion of the distal end melts and cures over the one or more echogenic components. Thus, the portion of the distal end that melts over the one or more echogenic components shields the echogenic components from a patient.

In one embodiment, the portion of the distal end that melts over the one or more echogenic components forms a seal with the one or more echogenic components such that air is eliminated between the catheter and the discontinuities of the one or more echogenic components. In another embodiment, the method may further include placing the one or more echogenic components at the distal end of the catheter.

In further embodiments, the catheter may include an open distal tip. Alternatively, the method may include clamping or sealing (e.g. heat sealing) the distal end of the catheter to form a closed distal tip. In still another embodiment, a thickness of the portion of the distal end that melts over the one or more echogenic components may range from about 0.01 millimeter (mm) to about 0.5 mm, more preferably from about 0.02 mm to about 0.25 mm.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of an ultrasonic catheter assembly according to the present disclosure;

FIG. 2 illustrates a cross-sectional view of the catheter assembly of FIG. 1 along line 2-2;

FIG. 3 illustrates a perspective view of another embodiment of an ultrasonic catheter assembly according to the present disclosure;

FIG. 4 illustrates a cross-sectional view of the catheter assembly of FIG. 3 along line 4-4;

FIG. 5 illustrates a cross-sectional view of one embodiment of an ultrasonic catheter assembly according to the present disclosure, particularly illustrating the closed distal end of the catheter assembly having a plurality of piezoelectric elements;

FIG. 6 illustrates a cross-sectional view of another embodiment of an ultrasonic catheter assembly according to the present disclosure, particularly illustrating the open distal end of the catheter assembly having a plurality of piezoelectric elements;

FIG. 7 illustrates a cross-sectional view of yet another embodiment of an ultrasonic catheter assembly according to the present disclosure, particularly illustrating the distal end of the catheter assembly having a piezoelectric catheter plug flush with the distal end;

FIG. 8 illustrates a cross-sectional view of still another embodiment of an ultrasonic catheter assembly according to the present disclosure, particularly illustrating the distal end of the catheter assembly having a piezoelectric catheter plug recessed from the distal end;

FIG. 9 illustrates a cross-sectional view of another embodiment of an ultrasonic catheter assembly according to the present disclosure, particularly illustrating the distal end of the catheter assembly having a piezoelectric catheter plug;

FIG. 10 illustrates a cross-sectional view of one embodiment of an ultrasonic catheter assembly according to the present disclosure, particularly illustrating the distal end of the catheter assembly having a piezoelectric or echogenic catheter band;

FIG. 11 illustrates a side view of another embodiment of an ultrasonic catheter assembly according to the present disclosure, particularly illustrating an echogenic catheter band configured around the outer diameter of an open tip catheter;

FIG. 12 illustrates a cross-sectional view of the catheter assembly of FIG. 11 along line 12-12;

FIG. 13 illustrates a side view of another embodiment of an ultrasonic catheter assembly according to the present disclosure, particularly illustrating an echogenic catheter band configured around the outer diameter of the closed tip catheter, wherein a portion of the catheter is melted over the echogenic band;

FIG. 14 illustrates a cross-sectional view of the catheter assembly of FIG. 13 along line 14-14;

FIG. 15 illustrates a cross-sectional view of another embodiment of an ultrasonic catheter assembly according to the present disclosure, particularly illustrating an open distal end of the catheter having a piezoelectric or echogenic catheter band configured thereon;

FIG. 16 illustrates a cross-sectional view of one embodiment of an ultrasonic catheter assembly according to the present disclosure, particularly illustrating the closed distal end of the catheter having a plurality of piezoelectric graphene strips;

FIG. 17 illustrates a cross-sectional view of one embodiment of an ultrasonic catheter assembly according to the present disclosure, particularly illustrating the closed distal end of the catheter having portions of the catheter formed from one or more graphene sections;

FIG. 18 illustrates a cross-sectional view of one embodiment of an ultrasonic catheter assembly according to the present disclosure, particularly illustrating the distal end of the catheter having a piezoelectric catheter tip configured therein; and FIG. 19 illustrates a flow diagram of one embodiment of a method for manufacturing an ultrasonic catheter assembly according to the present disclosure.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the connector is the end oriented towards a catheter insertion site), and "proximal" refers to the opposite direction (e.g., the proximal end of the catheter is inserted into the distal end of the connector).

Generally, the present disclosure is directed to an active ultrasonic or echogenic catheter assembly. More specifically, the catheter assembly includes a catheter and one or more piezoelectric or echogenic components. The catheter has a side wall that extends from a proximal end and a distal end that defines a lumen extending from the proximal end to the distal end. Thus, the lumen is configured to deliver a treatment fluid from the proximal end to the distal end. In addition, the piezoelectric or echogenic component(s) are configured with the inner surface of the side wall of the catheter and/or are embedded at least partially within the side wall of the catheter. As such, the piezoelectric or echogenic component(s) are configured to enhance ultrasonic imaging of the catheter, e.g. when activated by a stimulator assembly.

Referring now to the drawings, FIGS. 1-18 illustrate various embodiments of an ultrasonic catheter assembly 10 according to the present disclosure. It should be understood that the catheter assembly of the present disclosure may have any suitable catheter configuration known in the art. For example, in certain embodiments, the catheter assembly may be used with a through-the-needle catheter. Alternatively, the catheter assembly may be used with an over-the-needle catheter. For example, as shown in FIG. 1, the catheter assembly 10 may be an over-the-needle (OTN) catheter assembly having a catheter 14 with a proximal end 22 and a distal end 24 coaxially mounted onto a needle 12. Thus, the catheter assembly 10 may be configured such that the catheter 14 and needle 12 can be simultaneously inserted into a patient. In addition, as shown in FIGS. 2 and 4, the catheter 14 defines a side wall 18 that extends from the proximal end 22 and the distal end 24. Further, as shown, the side wall 18 has an inner surface 20 that defines a lumen 26 extending from the proximal end 22 to the distal end 24. Thus, the lumen 26 is configured to deliver a treatment fluid from the proximal end 22 of the catheter 14 to the distal end 12 to a treatment site of the patient, e.g. for the purposes of nerve block.

Still referring to FIG. 1, the catheter assembly 10 may also include an open distal tip 28, e.g. for delivering the treatment fluid and/or such that the needle 12 may extend beyond the open distal tip 28. In addition, the proximal end 22 of the catheter 14 may include a hub 16 configured thereon for mating communication with a fluid delivery device (not shown) such that a treatment fluid can be delivered to a targeted site within a patient via the lumen 26 and the open distal tip 28 of the catheter 14. In addition, it should also be understood that the catheter assembly 10 as described herein may optionally include one or more infusion holes for administering a treatment fluid to a patient. The fluid delivery device as described herein may be any suitable device known in the art, such as a pump, reservoir, syringe, or the like. Further, the hub 16 may have any conventional configuration, such as a Luer-lock fitting.

Referring particularly to FIG. 2, a perspective view of another embodiment of catheter assembly 10 according to the present disclosure is illustrated. For example, as shown, the catheter 14 may have a closed distal tip 29 (rather than an open distal tip 28 as shown in FIG. 1). In such an embodiment, the catheter 14 may contain one or more infusion holes 25 configured to deliver a treatment fluid to a targeted site within a patient via the lumen 26 of the catheter 14.

As shown generally in FIGS. 5-18, the ultrasonic catheter assembly 10 also includes one or more piezoelectric or echogenic components 30 configured to enhance ultrasonic imaging of the catheter assembly 10. As used herein a "piezoelectric component" or similar generally refers to a component that accumulates an electric charge in response to applied mechanical stress. Further, an "echogenic component" or similar generally refers to a component that is capable of bouncing an echo, i.e. returning a signal during an ultrasound procedure. More specifically, as shown, the piezoelectric or echogenic component(s) 30 may be embedded at the distal end 24 of the catheter 14. In addition, the piezoelectric or echogenic component(s) 30 may be configured with the inner surface 20 of the lumen 26 of the catheter 14. More specifically, as shown in FIGS. 5-6 and 9-10, the piezoelectric or echogenic component(s) 30 may be embedded at least partially within the side wall 18 of the catheter 14. In addition, in certain embodiments, the component(s) 30 may be embedded within the side wall 18 of the catheter 14 such that the component(s) may be shielded from a patient when inserted therein, e.g. as shown generally in the figures. Thus, the piezoelectric or echogenic component(s) 30 are configured to enhance ultrasonic imaging of the catheter 14.

In certain embodiments, the piezoelectric component(s) 30 as described herein may have various forms and/or shapes and may be constructed from a variety of materials. For example, in certain embodiments, the piezoelectric component(s) 30 may include at least one of graphene, crystals, ceramics (e.g. ceramic crystals), or any other suitable piezoelectric material. In addition, the piezoelectric component(s) 30 may include a catheter tip, a catheter plug, a plurality of piezoelectric elements 32, a catheter band, or similar.

More specifically, as shown in FIGS. 5-6, the piezoelectric component(s) 30 may include a plurality of piezoelectric elements 32 arranged at the distal end 24 of the catheter 14 and embedded at least partially within the side wall 18 of the catheter 14. Additionally, the piezoelectric elements 32 may include any suitable shape. For example, in particular embodiments, the shape of the piezoelectric elements 32 may include one of or a combination of the following shapes: sphere, cylinder, cone, pyramid, prism, cube, cuboid, irregular, or any other suitable shape. As such, the material, as well as the shape, may improve the ultrasonic imaging of the piezoelectric elements 32.

In additional embodiments, as shown in FIGS. 7-9, the piezoelectric component(s) 30 may include a catheter plug 34. More specifically, as shown, the catheter plug 34 may be inserted into the distal end 24 of the catheter 14 to enhance ultrasonic imaging of the catheter 14. In certain embodiments, as shown in FIG. 7, the catheter plug 34 may be inserted into the distal end 24 of the catheter 14 such that the plug 34 is flush with the open distal tip 28 of catheter 14. Alternatively, as shown in FIG. 8, the catheter plug 34 may be inserted into the distal end 24 of the catheter 14 such that the plug 34 is recessed from the open distal tip 28 of catheter 14. In addition, the catheter plug 34 may be secured within the lumen 26 via a friction fit, adhesives, or similar. Alternatively, as shown in FIG. 9, the catheter plug 34 may be partially embedded within the side wall 18 of the catheter 14. In addition, the catheter plug 34, as shown, includes a generally solid cross-section such that the plug 34 does not allow treatment fluid to pass therethrough. In alternative embodiments, however, the catheter plug 34 may include a hollow cross-section so as to allow at least some treatment fluid to pass therethrough.

Referring now to FIGS. 10-15, the piezoelectric or echogenic component(s) 30 may include a catheter band 38 configured to fit coaxially around an outer diameter 23 of the catheter 14. More specifically, as shown, the catheter band 38 may be slid onto the outer diameter 23 of the catheter 14, e.g. at the distal end 24 of the catheter 13. In further embodiments, e.g. as shown in FIG. 10, the catheter band 38 may be optionally embedded at the distal end 24 thereof. Alternatively, the catheter band 38 may also be sized to fit within the lumen 26 of the catheter 14. In additional embodiments, as shown in FIG. 18, the piezoelectric or echogenic component(s) 30 may include a catheter tip 36. Further, the catheter tip 36 may be sized such that at least a portion thereof can be inserted into the lumen 26 of the catheter 14 so as to engage the inner surface 20 of the side wall 18.

Referring specifically to FIGS. 11-15, the catheter assembly 10 may include one or more echogenic components 30 configured around the outer diameter 23 of the catheter 14. Moreover, the echogenic component(s) 30 may include a plurality of discontinuities 40 configured on an outer surface thereof to enhance ultrasonic imaging. More specifically, in certain embodiments, the discontinuities 40 may have any suitable size and/or shape arranged in any suitable pattern so as to provide enhanced ultrasonic imagine. For example, the discontinuities 40 may be arranged in a predetermined pattern so as to enhance ultrasonic imaging. In one embodiment, the pattern may include organized rows and/or columns of discontinuities. Alternatively, the pattern of discontinuities 40 may be random. In addition, the discontinuities 40 may include at least one or more of the following: indentations, grooves, notches, recesses, threads, protrusions, or similar. More particularly, the discontinuities 40 may include flat bottoms and flat sides. In further embodiments, the discontinuities 40 may include a first spherical indentation and a second spherical indentation contained within the first indentation to enhance ultrasonic imaging. For example, U.S. Patent Application Publication No.: 2014/0378841 entitled "Echogenic Article with Compound Discontinuities" filed on Jun. 18, 2014 discloses suitable discontinuities that may be included on the echogenic member 30 of the present disclosure and is herein incorporated by reference in its entirety. In still further embodiments, the discontinuities 40 may include longitudinal or radial threads 62.

In further embodiments, the discontinuities 40 of the echogenic components 30 may be manufactured using any suitable means. For example, in certain embodiments, the discontinuities 40 may be manufactured using laser etching, spatter techniques (i.e. displacement of metal and/or other phenomena), cutting, machining, or similar. In still additional embodiments, the echogenic member 30 may be constructed of any suitable echogenic material. For example, in specific embodiments, the echogenic member 30 may be constructed of a metal or metal alloy. More particularly, the metal or metal alloy may include at least one of or a combination of the following: aluminum, titanium, copper, tin, nickel, zinc, magnesium, stainless steel, or similar.

In addition, after the echogenic(s) components 30 are slid onto the outer diameter 23 of the catheter 14 (FIGS. 11 and 12), the distal end 24 of the catheter 14 may be heated until a portion 46 of the distal end 24 melts and cures over the one or more echogenic components 30, e.g. as shown in FIGS. 13 and 14. Thus, the portion 46 of the distal end 24 that melts over the echogenic component(s) 30 is configured to shield the component(s) 30 from a patient. In addition, the thickness of the portion 46 of the distal end 24 that melts over the echogenic component(s) 30 may range from about 0.01 millimeter (mm) to about 0.5 mm, more preferably from about 0.02 mm to about 0.25 mm. More specifically, in certain embodiments, the portion 46 of the distal end 24 that melts over the one or more echogenic component(s) 30 may be configured to form a seal with the echogenic component(s) 30 such that air (e.g. air bubbles) is eliminated between the catheter 14 and the discontinuities 40 of the echogenic component(s) 30. As such, in particular embodiments, there are no gaps or air pockets between the film 46 and the echogenic component(s) 30. The absence of gaps and/or air pockets further enhances ultrasonic imaging of the catheter assembly 10. In addition, as shown in FIG. 11, the catheter assembly 10 may include an open distal tip 28. Alternatively, the catheter distal tip 24 may be clamped or sealed (e.g. heat sealed or fused) to form a closed distal tip 29, e.g. as shown in FIG. 12.

Referring now to FIGS. 17 and 18, the piezoelectric or echogenic component(s) 30 may also include a graphene coating, a graphene strip, or similar. For example, as shown in FIG. 17, the distal end 24 of the catheter 14 includes a plurality of graphene strips 42 or coatings applied to the inner surface 20 of the side wall 18. Further, it should be understood that the graphene strips 42 or coatings may have any suitable thickness so as to provide enhanced ultrasonic imaging of the distal end 24 of the catheter 14. Alternatively, as shown in FIG. 18, at least a portion 44 of the side wall 18 of the catheter 14 may be formed of graphene. Thus, by providing graphene in the catheter 14, the strength and conductivity of the catheter 14 is improved.

Referring now to FIG. 19, a flow diagram of one embodiment of a method 100 of manufacturing an ultrasonic catheter assembly is illustrated. As shown at 102, the method 100 includes forming a catheter 14 having a side wall 18 that extends from a proximal end 22 to a distal end 24. As mentioned, the side wall 18 defining an inner surface 20 that forms a lumen 26 extending from the proximal end 22 to the distal end 24 that is configured to deliver a treatment fluid therethrough. As shown at 104, the method 100 includes securing one or more piezoelectric components 30 with the distal end 24 of the catheter 14, wherein the one or more piezoelectric components 30 enhance ultrasonic imaging of the catheter 14. As such, in certain embodiments, the piezoelectric component(s) 30 are configured to contact at least a portion of the inner surface 20 of the catheter 14.

In one embodiment, the method 100 may further include embedding one or more of the piezoelectric components 30 into the side wall 18 of the catheter 14 at the distal end 24 thereof. More specifically, as mentioned, the piezoelectric component(s) 30 may include at least one of a catheter tip 36, a catheter plug 34, a plurality of piezoelectric elements 32, a catheter band 38, or similar. In additional embodiments, the step of embedding the piezoelectric component(s) 30 into the side wall 18 of the catheter 14 may also include placing the piezoelectric component(s) 30 onto the distal end 24 of the catheter 14 and heating the distal end 24 until a portion of the distal end 24 melts and cures over the piezoelectric component(s) 30, e.g. as shown in FIG. 10. As such, the portion of the distal end 24 of the catheter 14 that melts over the piezoelectric component(s) 30 (e.g. catheter band 38) is configured to shield the piezoelectric component(s) 30 from a patient.

In further embodiments, the step of arranging the piezoelectric component(s) 30 within the lumen 26 of the catheter 14 may further include applying a graphene coating, one or more graphene strips, or similar to the inner surface of the side wall of the catheter, e.g. as shown in FIGS. 17 and 18. In alternative embodiments, the step of arranging the piezoelectric component(s) 30 within the lumen 26 of the catheter 14 may further include inserting the piezoelectric component(s) 30 (e.g. the catheter tip 26, the catheter plug 34, the catheter band 38, or similar) within the distal end 24 of the catheter 14 such that the piezoelectric component(s) 30 contacts the inner surface 28 of the side wall 18 of the catheter 14.

In additional embodiments, the method 100 may also include activating, via a stimulator assembly 50, the piezoelectric component(s) 30 when the catheter 14 is inserted into a patient. For example, as shown in FIGS. 1 and 2, the stimulator assembly 50 may be configured to apply heat to the catheter 14. For example, as shown, the stimulator assembly 50 may be coupled with the hub 16 of the catheter 14 so as to apply heat or current to the catheter 14 so as to activate the piezoelectric components as described herein. In further embodiments, the stimulator assembly 50 may be directly coupled to the catheter 14 (or the needle 12 where applicable) or any other suitable component of the catheter assembly 10. Further, the stimulator assembly 50 may correspond to a nerve stimulator apparatus having a nerve stimulator 52 that provides heat or current through one or more stimulator wires 54. It should be understood, however, that the stimulator assembly 50 can further include any other suitable heating assembly known in the art and the illustrated embodiment is provided for illustrative purposes only. For example, in further embodiments, the stimulator assembly 50 may also include one or more battery devices, temperature-controlled water, an ultrasound device, a vibration device, or similar.

In still another embodiment, the method of manufacturing an ultrasonic catheter assembly may include forming a catheter 14 having a side wall 18 that extends from a proximal end 22 to a distal end 24. As mentioned, the side wall 18 defines an inner surface 20 that forms a lumen 26 extending from the proximal end 22 to the distal end 24 that is configured to deliver a treatment fluid therethrough. Thus, as shown in FIGS. 10, 11, and 15, the method may also include placing one or more echogenic components 30 onto the distal end 24 of the catheter 14 and heating the distal end 24 of the catheter 14 until a portion 33 of the distal end 24 melts and cures over the one or more echogenic components 30. Thus, the portion 33 of the distal end 24 that melts over the one or more echogenic components 30 shields the echogenic components 30 from a patient.

In certain embodiments of the method of the present invention, the catheter 14 may have a side wall 18 that extends from a proximal end 22 to a distal end 24. The side wall 18 defines an inner surface 20 that forms a lumen 26 extending from the proximal end 22 to the distal end 24 that is sealed or closed (not shown) by heating the distal end 24. Liquid may be delivers through small holes in the sidewall (not shown) near the distal end 24 of the catheter 14. Examples of such configurations may be found at, for example, U.S. Pat. Nos. 7,465,291; 7,438,711; 7,527,609; 7,569,045; and 8,328,771, the contents of which are incorporated by reference.

In addition to shielding the echogenic component 30 from the tissue of a patient, another important aspect of the process of melting the portion 33 of the distal end 24 of the catheter 14 over the echogenic components 30 is encountered when the exterior surface of the echogenic component(s) 30 includes a plurality of discontinuities 40 configured thereon to enhance ultrasonic imaging as described above. More specifically, in certain embodiments, when such discontinuities 40 are present, it is important that the process of melting the portion 33 of the distal end 24 of the catheter occur in such a way that eliminates or avoids the presence of air pockets, gaps or voids in discontinuities 40 that are filled by the melted material filling in the discontinuities 40. The presence of such air pockets, gaps or voids is undesirable and notably attenuates or diminishes the ultrasound energy reflecting from the ultrasonic component at the discontinuities 40.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An ultrasonic over-the-needle catheter assembly, comprising:
   a conductive needle;
   a catheter mounted coaxially around the conductive needle, the catheter comprising a side wall that extends from a proximal end to a distal end having a distal-most tip, the side wall defining a lumen extending from the proximal end to the distal end, the lumen configured to deliver a treatment fluid from the proximal end to the distal end;
   one or more wireless piezoelectric bands positioned circumferentially around the lumen and embedded within the side wall of the lumen of the catheter, wherein the one or more wireless piezoelectric bands comprise a plurality of discontinuities configured to enhance ultrasonic imaging of the catheter, wherein the discontinuities comprises at least one or more of the following: etchings, indentations, grooves, notches, or recesses; and
   a stimulator assembly for activating the one or more wireless piezoelectric bands through the conductive needle when the catheter is inserted into a patient,
   wherein a portion of the side wall of the catheter is melted and cured over the one or more wireless piezoelectric bands to define a shielding portion having a wall thickness greater than a wall thickness of remaining portions of the catheter, the shielding portion extending from the distal-most tip of the catheter to a location between the proximal end and the distal end of the catheter, wherein the shielding portion forms a seal with the discontinuities of the one or more wireless piezoelectric bands such that gaps or air pockets are minimized between the shielding portion and the one or more wireless piezoelectric bands.

2. The catheter assembly of claim 1, wherein the one or more wireless piezoelectric bands comprise at least one of graphene or one or more ceramic crystals.

3. The catheter assembly of claim 2, wherein the graphene comprises at least one of a graphene coating or a graphene strip.

4. The catheter assembly of claim 2, wherein the one or more ceramic crystals comprise any one of or a combination of the following shapes: sphere, cylinder, cone, pyramid, prism, cube, cuboid, or irregular, or ring-shaped.

* * * * *